(12) United States Patent
Woehr et al.

(10) Patent No.: US 10,166,370 B2
(45) Date of Patent: *Jan. 1, 2019

(54) CATHETER INSERTION DEVICE

(71) Applicant: B. Braun Melsungen AG, Melsungen (DE)

(72) Inventors: Kevin Woehr, Felsberg (DE); Kenneth C. Raines, Bethlehem, PA (US)

(73) Assignee: B. Braun Melsungen AG, Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/004,211

(22) Filed: Jun. 8, 2018

(65) Prior Publication Data

US 2018/0289931 A1 Oct. 11, 2018

Related U.S. Application Data

(63) Continuation of application No. 14/860,253, filed on Sep. 21, 2015, which is a continuation of application
(Continued)

(30) Foreign Application Priority Data

Jul. 4, 2002 (DE) .............................. 202 10 394 U (51) Int. Cl.
*A61M 25/06* (2006.01)
*A61B 17/34* (2006.01)
(Continued)

(52) U.S. Cl.
CPC ..... *A61M 25/0606* (2013.01); *A61B 17/3415* (2013.01); *A61M 25/0097* (2013.01);
(Continued)

(58) Field of Classification Search
CPC .......... A61M 25/0097; A61M 25/0606; A61M 25/0618; A61M 39/221; A61M 39/0693;
(Continued)

(56) References Cited

U.S. PATENT DOCUMENTS

| 3,585,996 A | 6/1971 | Reynolds et al. |
| 3,601,151 A | 8/1971 | Winnard |

(Continued)

FOREIGN PATENT DOCUMENTS

| AU | 730988 B2 | 3/2001 |
| AU | 2003246358 B2 | 1/2004 |

(Continued)

OTHER PUBLICATIONS

Statutory Declaration of Kevin Woehr, Executed on Sep. 15, 2011, In the matter of Australian Patent Application No. 2003246358 and in the matter of Opposition thereto by Terumo Corporation, including Exhibits KW-1 to KW-7 (101 pages).
(Continued)

*Primary Examiner* — Bhisma Mehta
*Assistant Examiner* — Hamza Darb
(74) *Attorney, Agent, or Firm* — Klein, O'Neill & Singh, LLP (57) ABSTRACT

Embodiments of a catheter insertion device are discussed comprising: an approximately hollow cylindrical catheter sleeve, at whose distal end a catheter is attached; a needle sleeve with a hollow needle, which is attached thereto and which, when ready for use, extends through the catheter sleeve and the catheter, and; a needle protective element that is arranged inside the catheter sleeve while being able to move on the needle. Said needle protective element has an engaging section that engages with an engaging device, which is formed in the vicinity of the needle tip, when the hollow needle is withdrawn from the catheter sleeve. A
(Continued)

check valve is placed inside the catheter sleeve between the catheter and the needle protective element. The hollow needle, when ready for use, extends through said check valve, and the check valve automatically closes once the needle is withdrawn.

30 Claims, 3 Drawing Sheets

Related U.S. Application Data

No. 14/161,169, filed on Jan. 22, 2014, now Pat. No. 9,149,626, which is a continuation of application No. 14/018,162, filed on Sep. 4, 2013, now Pat. No. 9,149,625, which is a continuation of application No. 13/630,251, filed on Sep. 28, 2012, now Pat. No. 8,540,728, which is a continuation of application No. 13/425,140, filed on Mar. 20, 2012, now Pat. No. 8,337,463, which is a continuation of application No. 12/790,630, filed on May 28, 2010, now Pat. No. 8,328,762, which is a continuation of application No. 10/520,325, filed as application No. PCT/EP03/07073 on Jul. 2, 2003, now Pat. No. 7,736,339.

(51) Int. Cl.
A61M 25/00 (2006.01)
A61M 39/22 (2006.01)
A61M 5/32 (2006.01)
A61M 39/06 (2006.01)

(52) U.S. Cl.
CPC .... *A61M 25/0618* (2013.01); *A61M 39/0693* (2013.01); *A61M 39/221* (2013.01); *A61M 5/3273* (2013.01); *A61M 39/0606* (2013.01); *A61M 2005/325* (2013.01); *Y10T 29/49826* (2015.01)

(58) Field of Classification Search
CPC ............ A61M 5/3273; A61M 39/0606; A61M 2005/325; A61B 17/3415; Y10T 29/49826
See application file for complete search history.

(56) References Cited

U.S. PATENT DOCUMENTS

| | | |
|---|---|---|
| 3,620,500 A | 11/1971 | Santomieri |
| 3,662,754 A | 5/1972 | Halloran |
| 3,727,613 A | 4/1973 | Sorenson et al. |
| 4,143,853 A | 3/1979 | Abramson |
| 4,387,879 A | 6/1983 | Tauschinski |
| 4,449,693 A | 5/1984 | Gereg |
| 4,511,359 A | 4/1985 | Vaillancourt |
| 4,512,766 A | 4/1985 | Vailancourt |
| 4,578,063 A | 3/1986 | Inman et al. |
| 4,673,399 A | 6/1987 | Pruett |
| 4,683,916 A | 8/1987 | Raines |
| 4,762,516 A | 8/1988 | Luther et al. |
| 4,765,588 A | 8/1988 | Atkinson |
| 4,772,266 A | 9/1988 | Groshong |
| 4,790,828 A | 12/1988 | Dombrowski et al. |
| 4,795,432 A | 1/1989 | Karczmer |
| 4,813,938 A | 3/1989 | Raulerson |
| 4,842,591 A | 6/1989 | Luther |
| 4,846,809 A | 7/1989 | Sims |
| 4,846,811 A | 7/1989 | Vanderhoof |
| 4,850,961 A | 7/1989 | Wanderer et al. |
| 4,874,377 A | 10/1989 | Newgard et al. |
| 4,883,461 A | 11/1989 | Sawyer |
| 4,917,668 A | 4/1990 | Haindl |
| 4,927,414 A | 5/1990 | Kulli |
| 4,929,235 A | 5/1990 | Merry et al. |
| 4,929,241 A | 5/1990 | Kulli |
| 4,935,010 A | 6/1990 | Cox et al. |
| 4,944,725 A | 7/1990 | McDonald |
| 4,944,728 A | 7/1990 | Carrell et al. |
| 4,952,207 A | 8/1990 | Lemieux |
| 4,964,854 A | 10/1990 | Luther |
| 4,966,586 A | 10/1990 | Vaillancourt |
| 4,978,344 A | 12/1990 | Dombrowski et al. |
| 5,007,901 A | 4/1991 | Shields |
| 5,010,925 A | 4/1991 | Atkinson et al. |
| 5,051,109 A | 9/1991 | Simon |
| 5,053,014 A | 10/1991 | Van Heugten |
| 5,053,017 A | 10/1991 | Chamuel |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,098,393 A | 3/1992 | Amplatz et al. |
| 5,108,374 A | 4/1992 | Lemieux |
| 5,116,021 A | 5/1992 | Faust et al. |
| 5,127,905 A | 7/1992 | Lemieux |
| 5,135,489 A | 8/1992 | Jepson et al. |
| 5,135,504 A | 8/1992 | McLees |
| 5,147,327 A | 9/1992 | Johnson |
| 5,152,751 A | 10/1992 | Kozlowski |
| 5,154,703 A | 10/1992 | Bonaldo |
| 5,156,596 A | 10/1992 | Balbierz et al. |
| 5,158,554 A | 10/1992 | Jepson et al. |
| 5,180,370 A | 1/1993 | Gillespie |
| 5,183,468 A | 2/1993 | McLees |
| 5,188,607 A | 2/1993 | Wu |
| 5,195,980 A | 3/1993 | Catlin |
| 5,215,525 A | 6/1993 | Sturman |
| 5,215,528 A | 6/1993 | Purdy et al. |
| 5,234,410 A | 8/1993 | Graham et al. |
| 5,242,393 A | 9/1993 | Brimhall et al. |
| RE34,416 E | 10/1993 | Lemieux |
| 5,269,771 A | 12/1993 | Thomas et al. |
| 5,300,033 A | 4/1994 | Miller |
| 5,300,045 A | 4/1994 | Plassche, Jr. |
| 5,312,355 A | 5/1994 | Lee |
| 5,322,517 A | 6/1994 | Sircom et al. |
| 5,328,482 A | 7/1994 | Sircom et al. |
| 5,330,435 A | 7/1994 | Vaillancourt |
| 5,334,158 A | 8/1994 | McLees |
| 5,334,159 A | 8/1994 | Turkel |
| 5,334,161 A | 8/1994 | Gurmarnik |
| 5,344,408 A | 9/1994 | Partika |
| 5,348,544 A | 9/1994 | Sweeney et al. |
| 5,352,205 A | 10/1994 | Dales et al. |
| 5,380,305 A | 1/1995 | Ghouri |
| 5,405,323 A | 4/1995 | Rogers et al. |
| 5,405,336 A | 4/1995 | Austin et al. |
| 5,409,461 A | 4/1995 | Steinman |
| 5,419,766 A | 5/1995 | Chang et al. |
| 5,423,766 A | 6/1995 | Di Cesare |
| 5,423,799 A | 6/1995 | Shin |
| 5,454,790 A | 10/1995 | Dubrul |
| 5,456,675 A | 10/1995 | Wolbring et al. |
| 5,458,640 A | 10/1995 | Gerrone |
| 5,458,658 A | 10/1995 | Sircom |
| 5,487,728 A | 1/1996 | Vaillancourt |
| 5,501,675 A | 3/1996 | Erskine |
| 5,538,508 A | 7/1996 | Steyn |
| 5,558,651 A | 9/1996 | Crawford et al. |
| 5,562,630 A | 10/1996 | Nichols |
| 5,562,633 A | 10/1996 | Wozencroft |
| 5,573,516 A | 12/1996 | Tyner |
| 5,584,809 A | 12/1996 | Gaba |
| 5,601,536 A | 2/1997 | Crawford et al. |
| 5,613,663 A | 3/1997 | Schmidt et al. |
| 5,634,913 A | 6/1997 | Stinger |
| 5,651,772 A | 7/1997 | Arnett |
| 5,662,610 A | 9/1997 | Sircom |
| 5,688,253 A | 11/1997 | Paradis |
| 5,697,907 A | 12/1997 | Gaba |
| 5,718,688 A | 2/1998 | Wozencroft |
| 5,725,503 A | 3/1998 | Arnett |
| 5,738,144 A | 4/1998 | Rogers |

(56) References Cited

U.S. PATENT DOCUMENTS

| | | |
|---|---|---|
| 5,749,857 A | 5/1998 | Cuppy |
| 5,749,859 A | 5/1998 | Powell |
| 5,755,709 A | 5/1998 | Cuppy |
| 5,779,681 A | 7/1998 | Bonn |
| D397,434 S | 8/1998 | Pike |
| 5,792,122 A | 8/1998 | Brimhall et al. |
| 5,817,069 A | 10/1998 | Arnett |
| 5,830,189 A | 11/1998 | Chang |
| 5,843,046 A | 12/1998 | Motisi et al. |
| 5,851,196 A | 12/1998 | Arnett |
| 5,853,393 A | 12/1998 | Bogert |
| 5,858,002 A | 1/1999 | Jesch |
| 5,865,806 A | 2/1999 | Howell |
| 5,879,337 A | 3/1999 | Kuracina et al. |
| 5,911,705 A | 6/1999 | Howell |
| 5,911,710 A | 6/1999 | Barry et al. |
| 5,935,104 A | 8/1999 | Janek et al. |
| 5,954,698 A | 9/1999 | Pike |
| 5,961,497 A | 10/1999 | Larkin |
| 5,967,490 A | 10/1999 | Pike |
| 5,971,957 A | 10/1999 | Luther et al. |
| 6,001,080 A | 12/1999 | Kuracina et al. |
| 6,004,294 A | 12/1999 | Brimhall et al. |
| 6,077,244 A | 6/2000 | Botich et al. |
| 6,080,137 A | 6/2000 | Pike |
| 6,117,108 A | 9/2000 | Woehr et al. |
| 6,171,287 B1 | 1/2001 | Lynn et al. |
| 6,203,527 B1 | 3/2001 | Zadini et al. |
| 6,213,978 B1 | 4/2001 | Voyten |
| 6,221,047 B1 | 4/2001 | Greene et al. |
| 6,228,060 B1 | 5/2001 | Howell |
| 6,273,869 B1 | 8/2001 | Vaillancourt |
| 6,287,278 B1 | 9/2001 | Woehr et al. |
| 6,322,537 B1 | 11/2001 | Chang |
| 6,352,520 B1 | 3/2002 | Miyazaki |
| 6,379,333 B1 | 4/2002 | Brimhall et al. |
| 6,379,372 B1 | 4/2002 | Dehdashtian et al. |
| 6,443,927 B1 | 9/2002 | Cook |
| 6,443,929 B1 | 9/2002 | Kuracina et al. |
| 6,485,468 B2 | 11/2002 | Vojtasek |
| 6,506,181 B2 | 1/2003 | Meng et al. |
| 6,533,759 B1 | 3/2003 | Watson et al. |
| 6,585,704 B2 | 7/2003 | Luther et al. |
| 6,595,954 B1 | 7/2003 | Luther et al. |
| 6,595,955 B2 | 7/2003 | Ferguson et al. |
| 6,616,630 B1 | 9/2003 | Woehr et al. |
| 6,629,959 B2 | 10/2003 | Kuracina et al. |
| 6,652,486 B2 | 11/2003 | Bialecki et al. |
| 6,652,490 B2 | 11/2003 | Howell |
| 6,689,102 B2 | 2/2004 | Greene |
| 6,692,471 B2 | 2/2004 | Boudreaux |
| 6,695,814 B2 | 2/2004 | Greene |
| 6,695,817 B1 | 2/2004 | Fangrow, Jr. |
| 6,699,221 B2 | 3/2004 | Vaillancourt |
| 6,709,419 B2 | 3/2004 | Woehr |
| 6,719,726 B2 | 4/2004 | Meng et al. |
| 6,749,588 B1 | 6/2004 | Howell et al. |
| 6,764,468 B1 | 7/2004 | East |
| 6,860,871 B2 | 3/2005 | Kuracina et al. |
| 6,883,778 B1 | 4/2005 | Newton et al. |
| 6,902,546 B2 | 6/2005 | Ferguson |
| 6,916,311 B2 | 7/2005 | Vojtasek |
| 6,958,055 B2 | 10/2005 | Donnan et al. |
| 6,972,002 B2 | 12/2005 | Thorne |
| RE38,996 E | 2/2006 | Crawford et al. |
| 7,008,404 B2 | 3/2006 | Nakajima |
| 7,125,396 B2 | 10/2006 | Leinsing et al. |
| 7,374,554 B2 | 5/2008 | Menzi et al. |
| 7,500,965 B2 | 3/2009 | Menzi et al. |
| 7,524,306 B2 | 4/2009 | Botich et al. |
| 7,635,352 B2 | 12/2009 | Adams |
| 7,651,476 B2 | 1/2010 | Kohler |
| 7,736,339 B2 | 6/2010 | Woehr et al. |
| 7,959,613 B2 | 6/2011 | Rhad et al. |
| 8,079,979 B2 | 12/2011 | Moorehead |
| 8,308,691 B2 | 11/2012 | Woehr et al. |
| 8,328,762 B2 | 12/2012 | Woehr et al. |
| 8,333,735 B2 | 12/2012 | Woehr et al. |
| 8,337,463 B2 * | 12/2012 | Woehr ............ A61M 25/0618 604/164.08 |
| 8,382,718 B2 | 2/2013 | Woehr |
| 8,460,247 B2 | 6/2013 | Woehr et al. |
| 8,469,928 B2 | 6/2013 | Stout et al. |
| 8,540,728 B2 | 9/2013 | Woehr et al. |
| 8,597,249 B2 | 12/2013 | Woehr et al. |
| 9,149,626 B2 | 10/2015 | Woehr et al. |
| 2001/0004686 A1 | 6/2001 | Huet |
| 2001/0041872 A1 | 11/2001 | Paul, Jr. |
| 2001/0053895 A1 | 12/2001 | Vaillancourt |
| 2002/0128604 A1 * | 9/2002 | Nakajima ........ A61M 39/0693 604/164.01 |
| 2002/0128605 A1 | 9/2002 | Miller et al. |
| 2002/0169418 A1 | 11/2002 | Menzi et al. |
| 2003/0060771 A1 | 3/2003 | Bialecki et al. |
| 2003/0199827 A1 | 10/2003 | Thorne |
| 2004/0044313 A1 | 3/2004 | Nakajima |
| 2004/0116856 A1 | 6/2004 | Woehr et al. |
| 2004/0225260 A1 | 11/2004 | Villa et al. |
| 2005/0043684 A1 | 2/2005 | Basta et al. |
| 2005/0075609 A1 | 4/2005 | Latona |
| 2005/0182363 A1 | 8/2005 | Kulli |
| 2006/0155245 A1 | 7/2006 | Woehr |
| 2006/0178635 A1 | 8/2006 | Callaway |
| 2006/0200080 A1 | 9/2006 | Abulhaj |
| 2007/0038182 A1 | 2/2007 | Bialecki et al. |
| 2007/0038186 A1 | 2/2007 | Sutton et al. |
| 2007/0196414 A1 | 8/2007 | Hammarsten et al. |
| 2014/0135702 A1 | 5/2014 | Woehr et al. |
| 2016/0008580 A1 * | 1/2016 | Woehr ............ A61M 25/0618 604/164.08 |

FOREIGN PATENT DOCUMENTS

| | | |
|---|---|---|
| AU | 783650 B2 | 11/2005 |
| CA | 2133053 | 3/1995 |
| DE | 2817102 | 10/1979 |
| DE | 30 00 903 A1 | 1/1980 |
| DE | 31 00 622 A1 | 4/1980 |
| DE | 32 10 148 A1 | 9/1983 |
| DE | 44 34 569 A1 | 3/1995 |
| DE | 691 15 064 | 8/1996 |
| DE | 195 45 452 | 11/1996 |
| DE | 196 39 870 | 12/1997 |
| DE | 299 21 084 | 2/2000 |
| DE | 199 15 342 | 10/2000 |
| DE | 199 55 445 | 6/2001 |
| DE | 201 04 539 U1 | 1/2002 |
| DE | 695 28 043 | 5/2003 |
| EP | 0352928 | 1/1990 |
| EP | 0 414 997 A1 | 4/1990 |
| EP | 0475375 | 3/1992 |
| EP | 0 554 841 A1 | 8/1993 |
| EP | 0 747 084 A2 | 12/1996 |
| EP | 0747085 | 12/1996 |
| EP | 0 799 626 A1 | 10/1997 |
| EP | 1 101 508 A2 | 5/2001 |
| EP | 1 101 508 A3 | 8/2001 |
| EP | 1 180 381 A1 | 2/2002 |
| EP | 0 746 359 | 9/2002 |
| EP | 1 240 916 B1 | 9/2002 |
| EP | 1 374 942 A1 | 1/2004 |
| EP | 1 374 942 B1 | 1/2004 |
| EP | 1 003 588 | 11/2004 |
| EP | 1 545 681 | 1/2008 |
| EP | 1 911 485 | 4/2008 |
| EP | 2292925 | 3/2011 |
| ES | 2254280 | 6/2006 |
| FR | 2794591 | 12/2000 |
| GB | 2 118 440 A | 11/1983 |
| GB | 2292925 | 3/1996 |
| JP | 6-154236 A | 6/1994 |
| JP | H07-503172 | 4/1995 |
| JP | 8-219314 A | 8/1996 |
| JP | 09-099096 A | 4/1997 |

(56) References Cited

FOREIGN PATENT DOCUMENTS

| JP | H10-57497 | 3/1998 |
|---|---|---|
| JP | 2000-504973 | 4/2000 |
| JP | 2001-514943 | 9/2001 |
| JP | 2002-000727 A | 1/2002 |
| JP | 2002102345 | 4/2002 |
| JP | 2002-126080 | 5/2002 |
| WO | WO 90/12606 | 11/1990 |
| WO | WO 93/05840 | 4/1993 |
| WO | WO 1995/022364 | 8/1995 |
| WO | WO 97/45151 | 12/1997 |
| WO | WO 98/30268 | 7/1998 |
| WO | WO 98/53875 | 12/1998 |
| WO | WO 99/08742 | 2/1999 |
| WO | WO 99/26682 | 6/1999 |
| WO | WO 01/07103 | 2/2001 |
| WO | WO 2001/012249 | 2/2001 |
| WO | WO 03/011381 A1 | 2/2003 |
| WO | WO 03/011383 | 2/2003 |
| WO | WO 2004/004819 A1 | 1/2004 |

OTHER PUBLICATIONS

Statutory Declaration of William Samuel Hunter, Executed and Notarized on May 11, 2010, In the matter of Australian Patent Application No. 2003246358 and in the matter of Opposition thereto by Terumo Corporation (43 pages).
Statutory Declaration of Noel J. Akers, Executed and Notarized on Aug. 17, 2011, In the matter of Australian Patent Application No. 2003246358, including Exhibit NJA-1 (48 pages).
Annex 1: Facts and Arguments to the Notice of Opposition to a European Patent; Opponent Smith Medical ASD Inc.; Patentee B. Braun Melsungen AG for Opposed Patent No. EP 1 545 681 B1; dated Oct. 21, 2008 (133 pages).
Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Jan. 27, 2011 (77 pages).
Response to Appeal and the Grounds for Appeal Filed by Patent Proprietor Against the Decision of the Opposition Division; Opponent Smith Medical ASD Inc.; Patentee B. Braun Melsungen AG for Opposed Patent No. EP 1 545 681 B1; dated Oct. 21, 2011 (86 pages).
Patent Abstracts of Japan; entitled "Indwelling Puncture Needle With Wing Having Branching Part", Application No. 11-021665, Publication No. 2000-217925; Published Aug. 8, 2000, Applicant Hanako Medical KK (3 pages).
Patent Abstracts of Japan; entitled "Safe Indwelling Needle", Application No. 2000-078335, Publication No. 2001-259029, Published Sep. 25, 2001, Applicant Medikit KK (7 pages).
Patent Abstracts of Japan; entitled "Safety Indwelling Needle", Application No. 2000-182911, Publication No. 2002-000727, Published Jan. 8, 2002, Applicant Medikit KK (4 pages).
Patent Abstracts of Japan; entitled "Indwelling Needle Structure", Applicant No. 2001-363865, Publication No. 2003-175112, Published Jun. 24, 2003, Applicant Mitsubishi Pencil Co LTD (5 pages).
Patent Abstracts of Japan; entitled "Indwelling Needle Structure and Seal Material Used Therefore", Application No. 2005-035112, Publication No. 2005-261938 A, Published Sep. 29, 2005, Applicant JMS Co LTD (5 pages).
Patent Abstracts of Japan; entitled "Indwelling Needle", Application No. 2004-143931, Publication No. 2005-323762, Published Nov. 24, 2005, Applicant Medikit KK (4 pages).
Patent Abstracts of Japan; entitled "Indwelling Needle", Application No. 1996-0040652, Publication No. 9206375, Published Aug. 12, 1997, Applicant: Togo Medikit KK (2 pages).
"Conical Fittings With 6% (Luer) Taper for Syringes, Needles and Certain Other Medical Euipment—Part 2: Lock fittings," International Standar, ISO 594-2, second edition, 1998, pp. 1-11, Technical Committee ISO/TC 84, Switzerland.

Office Action dated May 29, 2007 from corresponding U.S. Appl. No. 10/520,325, filed Sep. 12, 2005.
Final Office Action dated Nov. 14, 2007 from corresponding U.S. Appl. No. 10/520,325, filed Sep. 12, 2005.
Office Action dated Sep. 26, 2008 from corresponding U.S. Appl. No. 10/520,325, filed Sep. 12, 2005.
Final Office Action dated Mar. 30, 2009 from corresponding U.S. Appl. No. 10/520,325, filed Sep. 12, 2005.
Final Office Action dated Jan. 19, 2010 from corresponding U.S. Appl. No. 10/520,325, filed Sep. 12, 2005.
Notice of Allowance dated Feb. 25, 2010 from corresponding U.S. Appl. No. 10/520,325, filed Sep. 12, 2005.
Office Action dated Jun. 21, 2011 from corresponding U.S. Appl. No. 12/790,630, filed May 28, 2010.
Office Action dated Aug. 8, 2011 from corresponding U.S. Appl. No. 12/790,630, filed May 28, 2010.
Office Action dated Oct. 9, 2012 from corresponding U.S. Appl. No. 12/790,630, filed May 28, 2010.
Notice of Allowance dated Nov. 7, 2012 from corresponding U.S. Appl. No. 12/790,630, filed May 28, 2010.
Office Action dated Oct. 10, 2012 from corresponding U.S. Appl. No. 13/425,140, filed Mar. 20, 2012.
Notice of Allowance dated Nov. 7, 2012 from corresponding U.S. Appl. No. 13/425,140, filed Mar. 20, 2012.
Office Action dated Mar. 22, 2013 from corresponding U.S. Appl. No. 13/630,251, filed Sep. 28, 2013.
Notice of Allowance dated Jun. 20, 2013 from corresponding U.S. Appl. No. 13/630,251, filed Sep. 28, 2013.
Office Action dated Aug. 29, 2013 from corresponding U.S. Appl. No. 13/630,251, filed Sep. 28, 2013.
Re-Examination Report dated Aug. 30, 2013 from related Australian Application No. 2003246368 (5 pages).
Response to Re-Examination Report of Aug. 30, 2013, filed Oct. 3, 2013 from related Australian Application No. 2003246368 (8 pages).
Office Action dated Dec. 19, 2014 from corresponding U.S. Appl. No. 14/018,162, filed Sep. 4, 2013.
Office Action dated Dec. 26, 2014 from corresponding U.S. Appl. No. 12/161,169, filed Jan. 22, 2014.
First Office Action on corresponding foreign application (MX Application No. MX/a/2015/015133) from the Mexican Intellectual Property Office dated Aug. 4, 2017.
Second Office Action on corresponding foreign application (MX Application No. MX/a/2015/015134) from the Mexican Intellectual Property Office dated Aug. 14, 2017.
Official Action on corresponding foreign application (MX Application No. MX/a/2015/015133) from the Mexican Institute of the Industrial Property dated Jan. 23, 2018.
Official Action on corresponding foreign application (MX Application No. MX/a/2015/015134) from the Mexican Institute of the Industrial Property dated Jan. 31, 2018.
Official Action on corresponding foreign application (MX Application No. MX/a/2015/015136) from the Mexican Institute of the Industrial Property dated Feb. 8, 2018.
ISO 594-1, "Conical fittings with a 6% (Luer) taper for syringes, needles and certain other medical equipment—Part 1: General Requirements", International Standard (ISO), 594-1, First edition, Jun. 15, 1986, pp. 1-7.
David Holthaus, "Suppliers heed call for protective products", Hospitals, The Magazine for Health Care Executives, Sep. 20, 1987, pp. 72-73.
"Joint Advisory Notice: Department of Labor/Department of Health and Human Services; HBV/HIV", Federal Register, vol. 52, No. 210, Oct. 30, 1987, pp. 41818-41824.
Federal Register, Part II, Department of Labor, Occupational Safety and Health Administration, "Occupational Exposure to Bloodborne Pathogens; Final Rule", 29 CFR Part 1910.1030, vol. 56, No. 235, Dec. 6, 1991, 180 pages.
Chiarello et al., "N.Y. State, Department of Health, Pilot Study of Needlestick Prevention Devices, Report to the New York State Legislature", Mar. 1992, 73 pages, Part 1 of 2.
Chiarello et al., "N.Y. State, Department of Health, Pilot Study of Needlestick Prevention Devices, Report to the New York State Legislature", Mar. 1992, 77 pages, Part 2 of 2.

(56) References Cited

OTHER PUBLICATIONS

FDA Safety Alert, "Needlestick and Other Risks from Hypodermic Needles on Secondary I.V. Administration Sets—Piggyback and Intermittent I.V.", https://www.osha.gov/SLTC/bloodbornepathogens/fdaletter.html, Apr. 16, 1992.
Chiarello, "Selection of needlestick prevention devices: A conceptual framework for approaching product evaluation", American Journal of Infection Control, vol. 23, No. 6, Dec. 1995, pp. 386-395.
Judy Terry et al., "Intravenous Therapy Clinical Principles and Practice", W.B. Saunders Company, 1995, pp. 317-324.
ISO 10555-5, "Sterile, single-use intravascular catheters—Part 5: Over-needle peripheral catheters", International Standard (ISO) 10555-5, First edition, Jun. 15, 1996, pp. 1-14.
Lawrence F. Leslie et al, "Needle Puncture Resistance of Surgical Gloves, Finger Guards, and Glove Liners", Journal of Biomedical Materials Research (Applied Biomaterials), vol. 33, John Wiley & Sons, Inc., 1996, pp. 41-46.
Julie Steele, "Practical I.V. Therapy", $2^{nd}$ edition, Springhouse Corporation, Springhouse, Pennsylvania, 1996, pp. 27-56.
Hanrahan & Reutter, "A critical review of the literature on sharps injuries: epidemiology, management of exposures and prevention", Journal of Advanced Nursing, vol. 25, Blackwell Science, Ltd., 1997, pp. 144-154.
ECRI, "Needlestick-Prevention Devices", Health Devices, Oct. 1999, vol. 28, No. 10, 9 pages.
"Preventing Needlestick Injuries in Health Care Settings", National Institute for Occupational Safety and Health ("NIOSH") Alert issued by the Centers for Disease Control and Prevention ("CDC"), Pub No. 2000-108, Nov. 1999, 29 pages.
Claus M. Muth & Erik S. Shank, "Gas Embolism", The New England Journal of Medicine, vol. 342, No. 7, Massachusetts Medical Society, Feb. 17, 2000, pp. 476-482.
"Needlestick Safety and Prevention Act", Public Law No. 106-430, Nov. 6, 2000, 114 Stat. 1901-1905.
"Resilience", Stedman's Medical Dictionary, 27th Edition, Lippincott Williams & Wilkins, Balitimore, MD, 2000, 5 pages.
Centers for Disease Control and Prevention, "Updated U.S. Public Health Service Guidelines for the Management of Occupational Exposures to HBV, HCV, and HIV and Recommendations for Postexposure Prophylaxis", Morbidity and Mortality Weekly Report, U.S. Department of Health and Human Services, CDC, Atlanta, GA, vol. 50, No. RR-11, Jun. 29, 2001, 67 pages.
Judy Hankins, BSN, CRNI, et al., "Infusion Therapy in Clinical Practice", 2nd edition, W.B. Saunders Company, 2001, pp. 313-318; 344-347.
OSHA Fact Sheet, "OSHA's Bloodborne Pathogens Standard", U.S. Dept. of Labor Reference Guide, 2001, 2 pages.
OSHA, "Bloodborne Pathogens" Standard No. 1910.1030, 2001, 24 pages.
Lynn Dianne Phillips, "Manual of I.V. Therapeutics", $3^{rd}$ edition, F.A. Davis Company, Philadelphia, PA, 2001, 98 pages, Part 1.
Lynn Dianne Phillips, "Manual of I.V. Therapeutics", $3^{rd}$ edition, F.A. Davis Company, Philadelphia, PA, 2001, 111 pages, Part 2.
Weinstein, "Plumer's Principles & Practices of Intravenous Therapy", $7^{th}$ edition, Lippincott, 2001, Chapter 11, pp. 193-230.
Asai et al., "Efficacy of catheter needles with safeguard mechanisms", Anaesthesia, 2002, pp. 572-577, vol. 57, Blackwell Science Ltd.
Andrea Mummery, "Be sharp, be safe", Occupational Health, vol. 54, No. 9, Sep. 2002, 6 pages.
Saladow, "The use of vascular access devices with needle safety features", JVAD, Fall 2002, pp. 41-44.
Fran Powers, "Effectively Evaluating and Converting Your Organization to the Use of Infusion Safety Products", Journal of Infusion Nursing, vol. 25, No. 6S, Nov./Dec. 2002, pp. S10-S14.
Trim, JC, "A review of needle-protective devices to prevent sharps injuries", Clinical, British Journal of Nursing, vol. 13, No. 3, 2004, pp. 144-153.
FDA, Guidance for Industry and FDA Staff—"Medical Devices with Sharps Injury Prevention Features", U.S. Department of Health and Human Services, FDA, Center for Devices and Radiological Health, Aug. 9, 2005, pp. 1-17.
McKean, "Resilient", The New Oxford American Dictionary, second edition, Oxford University Press, 2005, 5 pages.
Rivera et al., "The history of peripheral intravenous catheters: How little plastic tubes revolutionized medicine", Acta Anaesthesiologica Belgica, vol. 56, No. 3, 2005, pp. 271-282.
U.S. Appl. No. 61/127,742 to Stephens, filed May 14, 2008, 45 pages.
Definition of "arm", www.engineering-dictionary.org, 2008.
B. Braun Introcan Safety IV Catheter, B. Braun Medical Inc., 2009.
"Top 10 Health Technology Hazards for 2011", Health Devices, vol. 39, Issue 11, Nov. 2010, ECRI Institute, pp. 386-398.
BD Saf-T-Intima, Beckton, Dickinson and Company, Jan. 2013.
OSHA—Compliance with bloodborne pathogens standard, Premier Safety Institute 2015, http://www.premiersafetyinstitute.org/safety-topics-az/needlestick-prevention/oshacompliance-with-bloodborne-pathogens-standard/.
B. Braun Interventional Systems Inc., Accel™ Valved Safety Centesis Catheter With Introcan Safety™ Technology, 2016.
BD Medical, BD Insyte Autoguard BC Shielded IV Catheter with Blood Control Technology, Beckton, Dickinson and Company, 2016.
B. Braun Medical Inc., MINI-SPIKE® Dispensing Pins, 2017, http://www.bbraunusa.com/products.html?prid=PRID00006971.
BD Insyte Autoguard Shielded IV Catheter, 2017, http://www.bd.com/en-us/offerings/capabilities/infusion/iv-catheters/bd-insyte-autoguard-shielded-iv-catheter.
The Medikit Supercath Z3V, http://www.medikit.co.jp/english/product/p1.html; 2017.
IPR Trial No. IPR2017-01586, U.S. Pat. No. 8,328,762; Petition for Inter Partes Review of Claims 18, 22, 25 of U.S. Pat. No. 8,328,762 Under 35 U.S.C. 312 and 37 C.F.R. 42.104; USPTO PTAB; *Becton, Dickinson and Company v. B. Braun Melsungen AG*; Jun. 16, 2017; 60 pages.
Case IPR2017-01586, U.S. Pat. No. 8,328,762 B2; Notice of Filing Date Accorded to Petition and Time for Filing Patent Owner Preliminary Response; USPTO PTAB; *Becton, Dickinson and Company v. B. Braun Melsungen AG*; Jun. 20, 2017; Paper No. 4; 5 pages.
Case IPR2017-01586, U.S. Pat. No. 8,328,762 B2; Decision Institution of Inter Partes Review 37 C.F.R. 42.108; USPTO PTAB; *Becton, Dickinson and Company v. B. Braun Melsungen AG*, Dec. 15, 2017; Paper No. 8; 39 pages.
IPR Trial No. IPR2017-01585, U.S. Pat. No. 8,337,463; Petition for Inter Partes Review of Claims 1, 2, 10, 12, 25, 28 of U.S. Pat. No. 8,337,463 Under 35 U.S.C. 312 and 37 C.F.R. 42.104; USPTO PTAB; *Becton, Dickinson and Company v. B. Braun Melsungen AG*; Jun. 16, 2017; 76 pages.
Case IPR2017-01585, U.S. Pat. No. 8,337,463 B2; Notice of Filing Date Accorded to Petition and Time for Filing Patent Owner Preliminary Response; USPTO PTAB; *Becton, Dickinson and Company v. B. Braun Melsungen AG*; Jun. 22, 2017; Paper No. 4; 5 pages.
Case IPR2017-01585, U.S. Pat. No. 8,337,463 B2; Decision Denying Institution of Inter Partes Review 37 C.F.R. 42.108; USPTO PTAB; *Becton, Dickinson and Company v. B. Braun Melsungen AG*; Dec. 15, 2017; Paper No. 8; 31 pages.
IPR Trial No. IPR2017-01583, U.S. Pat. No. 8,333,735; Petition for Inter Partes Review of Claims 1, 9, 10, 11, 18, 19, 24 of U.S. Pat. No. 8,333,735 Under 35 U.S.C. 312 and 37 C.F.R. 42.104; USPTO PTAB; *Becton, Dickinson and Company v. B. Braun Melsungen AG*; Jun. 16, 2017; 90 pages.
IPR Trial No. IPR2017-01583, U.S. Pat. No. 8,333,735; Declaration of Jack Griffis, III Regarding U.S. Pat. No. 8,333,735, Claims 1, 9, 10, 11, 18, 19, 24; USPTO PTAB; *Becton, Dickinson and Company v. B. Braun Melsungen AG*; Jun. 16, 2017; 282 pages.
Case IPR2017-01583, U.S. Pat. No. 8,333,735 B2; Notice of Filing Date Accorded to Petition and Time for Filing Patent Owner (56) References Cited

OTHER PUBLICATIONS

Preliminary Response; USPTO PTAB; *Becton, Dickinson and Company v. B. Braun Melsungen AG*; Jun. 20, 2017; Paper No. 4; 5 pages.
IPR Trial No. IPR2017-01584, U.S. Pat. No. 8,540,728; Petition for Inter Partes Review of Claims 1, 2, 9, 10, 24, 27, 28 of U.S. Pat. No. 8,540,728 Under 35 U.S.C. 312 and 37 C.F.R. 42.104; USPTO PTAB; *Becton, Dickinson and Company v. B. Braun Melsungen AG*; Jun. 16, 2017; 70 pages.
IPR Trial No. IPR2017-01584, U.S. Pat. No. 8,540,728; Declaration of Jack Griffis, III Regarding U.S. Pat. No. 8,540,728, Claims 1, 2, 9, 10, 24, 27, 28; USPTO PTAB; *Becton, Dickinson and Company v. B. Braun Melsungen AG*; Jun. 16, 2017; 182 pages.
Case IPR 2017-01584, U.S. Pat. No. 8,540,728 B2; Notice of Filing Date Accorded to Petition and Time for Filing Patent Owner Preliminary Response; USPTO PTAB; *Becton, Dickinson and Company v. B. Braun Melsungen AG*; Jun. 20, 2017; Paper No. 4; 5 pages.
IPR Trial No. IPR2017-01587, U.S. Pat. No. 9,149,626; Petition for Inter Partes Review of Claims 11, 20 of U.S. Pat. No. 9,149,626 Under 35 U.S.C. 312 and 37 C.F.R. 42.104; USPTO PTAB; *Becton, Dickinson and Company v. B. Braun Melsungen AG*; Jun. 16, 2017; 62 pages.
Case IPR2017-01587, U.S. Pat. No. 9,149,626 B2; Notice of Filing Date Accorded to Petition and Time for Filing Patent Owner Preliminary Response; USPTO PTAB; *Becton, Dickinson and Company v. B. Braun Melsungen AG*; Jun. 20, 2017; Paper No. 4; 5 pages.
IPR Trial No. IPR2017-01588, U.S. Pat. No. 8,460,247; Petition for Inter Partes Review of Claims 12, 13, 20, 22, 23, 29 of U.S. Pat. No. 8,460,247 Under 35 U.S.C. 312 and 37 C.F.R. 42.104; USPTO PTAB; *Becton, Dickinson and Company v. B. Braun Melsungen AG*; Jun. 16, 2017; 84 pages.
IPR Trial No. IPR2017-01588, U.S. Pat. No. 8,460,247; Declaration of Jack Griffis, III Regarding U.S. Pat. No. 8,460,247, Claims 12,13, 20-23, 29; USPTO PTAB; *Becton, Dickinson and Company v. B. Braun Melsungen AG*; Jun. 16, 2017; 118 pages.
Case IPR2017-01588, U.S. Pat. No. 8,460,247 B2; Notice of Filing Date Accorded to Petition and Time for Filing Patent Owner Preliminary Response; USPTO PTAB; *Becton, Dickinson and Company v. B. Braun Melsungen AG*; Jul. 21, 2017; Paper No. 6; 5 pages.
Case IPR2017-01588, U.S. Pat. No. 8,460,247 B2; Decision Institution of Inter Partes Review 37 C.F.R. 42.108; USPTO PTAB; *Becton, Dickinson and Company v. B. Braun Melsungen AG*, Dec. 21, 2017; Paper No. 8; 44 pages.
IPR Trial No. IPR2017-01589, U.S. Pat. No. 8,597,249; Petition for Inter Partes Review of Claims 1 and 4 of U.S. Pat. No. 8,597,249 Under 37 C.F.R. 312 and 37 C.F.R. 42,104; USPTO PTAB; *Becton, Dickinson and Company v. B. Braun Melsungen AG*; Jun. 16, 2017; 57 pages.
IPR Trial No. IPR2017-01589, U.S. Pat. No. 8,597,249; Declaration of Jack Griffis, III Regarding U.S. Pat. No. 8,597,249, Claims 1 and 4; USPTO PTAB; *Becton, Dickinson and Company v. B. Braun Melsungen AG*; Jun. 16, 2017; 78 pages.
Case IPR2017-01589, U.S. Pat. No. 8,597,249 B2; Notice of Filing Date Accorded to Petition and Time for Filing Patent Owner Preliminary Response; USPTO PTAB; *Becton, Dickinson and Company v. B. Braun Melsungen AG*; Jul. 21, 2017; Paper No. 6; 5 pages.
Case IPR2017-01589, U.S. Pat. No. 8,597,249 B2; Decision Institution of Inter Partes Review 37 C.F.R. 42.108; USPTO PTAB; *Becton, Dickinson and Company v. B. Braun Melsungen AG*, Jan. 12, 2018; Paper No. 8; 39 pages.
IPR Trial No. IPR2017-01590, U.S. Pat. No. 9,370,641; Petition for Inter Partes Review of Claims 15, 17, 18, 20, 22 of U.S. Pat. No. 9,370,641 Under 35 U.S.C. 312 and 37 C.F.R. 42.104; USPTO PTAB; *Becton, Dickinson and Company v. B. Braun Melsungen AG*; Jun. 16, 2017; 56 pages.
Case IPR2017-01590, U.S. Pat. No. 9,370,641 B2; Notice of Filing Date Accorded to Petition and Time for Filing Patent Owner Preliminary Response; USPTO PTAB; *Becton, Dickinson and Company v. B. Braun Melsungen AG*; Jul. 21, 2017; Paper No. 6; 5 pages.
Case IPR2017-01590, U.S. Pat. No. 9,370,641 B2; Decision Institution of Inter Partes Review 37 C.F.R. 42.108; USPTO PTAB; *Becton, Dickinson and Company v. B. Braun Melsungen AG*, Jan. 11, 2018; Paper No. 9; 30 pages.
Civil Action No. 1:16-cv-411-RGA; Memorandum Opinion; In the United States District Court for the District of Delaware; *B. Braun Melsungen AG, B. Braun Medical Industries SDN. BHD, and B. Braun Medical, Inc. v. Becton, Dickinson and Company and Becton, Dickinson Infusion Therapy Systems, Inc.*; Aug. 7, 2017; 24 pages.
Notice of Opposition to a European Patent, Oct. 21, 2008, European Patent Office, Opposed Patent No. EP 1 545 681, B. Braun Melsungen AG.
Submission of Proprietor, Feb. 4, 2013, Opposition Against EP 1 545 681.
Submission of Proprietor, Apr. 19, 2013, Opposition Against EP 1 545 681.
Expert Opinion by Dr. Hans Haindl dated Apr. 17, 2013 incl. Annexes I-III (BB2).
Submission of Proprietor, Feb. 18, 2014, Opposition Against EP 1 545 681.
Expert Opinion by Dr. Hans Haindl dated Feb. 16, 2014 incl Annexes 1 to 4a, 4b (BB3).
Excerpt from the internet "Devices that may Interfere with Pacemakers", 2013 (BB4).
Excerpt from the online medical textbook "Thieme", p. 1, paragraphs under titles "Inwiefern können elektronische Geräte einen Herzschrittmacher (HSM) beeinflussen?", "Inwiefern beeinflussen Handys Herzschrittmacher?", and „Wie können HSM durch Magnetfelder beeinflusst werden (BB5).
Decision in the amended version of the High Court of Malaya at Kuala Lumpur dated Jan. 8, 2013 (Civil Suit No. D-22IP-53-2010) (BB6).
Re-Examination Report dated Oct. 17, 2013 of AU 2003246358 (BB7 incl. attachment I).
Submission of Proprietor, Aug. 1, 2014, Opposition Against EP 1 545 681.
Affidavit by Greg Noonan dated Jul. 31, 2014 (BB15).
Product Sheet for SafSite (BB16).
Decision of Board of Appeal dated Oct. 8, 2014, rejecting appeal.
Search Report from DE Intellectual Property Office on corresponding DE application (202 10 394.3) dated Jun. 17, 2003.
AU Statement of Grounds and Particulars dated Feb. 19, 2010, Opposition to Patent Application No. 2003246358.
First Examination Report on corresponding foreign application (AU Application No. 2009238275) from the Australian Intellectual Property Office dated Feb. 14, 2012.
Notice of Acceptance on corresponding foreign application (AU Application No. 2009238275) from the Australian Intellectual Property Office dated Feb. 27, 2013.
English Translation of Office Action on corresponding foreign application (JP Application No. 2004-518674) from the Japan Patent Office dated Jun. 2, 2009.
Office Action on corresponding foreign application (MX Application No. PA/a/2004/012830) from the Mexican Patent Office dated Aug. 7, 2007.
Office Action on corresponding foreign application (MX Application No. PA/a/2004/012830) from the Mexican Patent Office dated Dec. 7, 2007.
Office Action on corresponding foreign application (MX Application No. PA/a/2004/012830) from the Mexican Patent Office dated Mar. 31, 2008.
Office Action on corresponding foreign application (MX Application No. MX/a/2008/007111) from the Mexican Patent Office dated Apr. 29, 2010.
Office Action on corresponding foreign application (MX Application No. MX/a/2010/012000) from the Mexican Patent Office dated Feb. 27, 2014.

(56) References Cited

OTHER PUBLICATIONS

Office Action on corresponding foreign application (MX Application No. MX/a/2013/002156) from the Mexican Patent Office dated Aug. 18, 2015.
First Examination Report on corresponding foreign application (AU Application No. 2013201814) from the Australian Intellectual Property Office dated Oct. 4, 2013.
First Examination Report on corresponding foreign application (AU Application No. 2016269475) from the Australian Intellectual Property Office dated Jul. 16, 2018.
First Examination Report on corresponding foreign application (AU Application No. 2016269477) from the Australian Intellectual Property Office dated Jul. 16, 2018.
Office Action on corresponding foreign application (MX Application No. MX/a/2015/015133) from the Mexican Intellectual Property Office dated Aug. 15, 2018.

* cited by examiner

CATHETER INSERTION DEVICE

FIELD

Device, system, and method for a catheter insertion device are generally discussed herein with specific reference to catheter device having a valve opener and a valve.

BACKGROUND

A device of this kind is known from EP 352 928, wherein in a hollow catheter hub a needle guard element is arranged. On withdrawal of the hollow needle from the catheter over an engaging means near the tip of the hollow needle, the needle guard element engages with the engaging means and covers the tip when the hollow needle is separated from the catheter. In this design, after withdrawal of the hollow needle from the catheter, through this catheter blood can issue with which the operating personnel can come into contact.

The invention is based on the object of designing a catheter insertion device of the type described above such that an outflow of blood from the catheter is prevented after removal of the hollow needle with the needle guard element.

SUMMARY

This object is solved according to the invention by the features in the characterizing part of claim 1. In the ready position, a check valve is arranged in the catheter hub between the catheter and the needle guard element. Through this valve the hollow needle extends, so that after withdrawal of the hollow needle from the catheter the latter can be reliably closed such that an outflow of blood is prevented, while simultaneously the tip of the hollow needle is securely covered by the needle guard element so that the operating personnel cannot injure themselves on the needle tip.

BRIEF DESCRIPTION OF THE DRAWINGS

Exemplary embodiments of the invention are explained in more detail below with reference to the drawing, in which.

DETAILED DESCRIPTION

Figure 1:
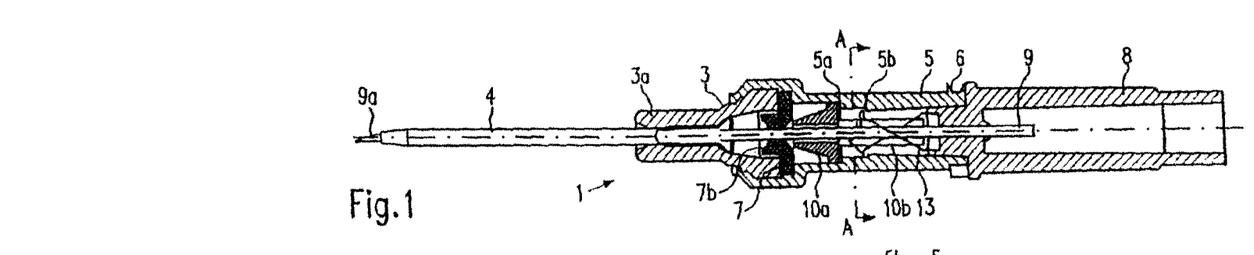
FIG. 1 shows a longitudinal section through a catheter insertion device in the ready position.

FIG. 1 shows a catheter insertion device 1 having a catheter hub 2 which has a two-part form in the embodiment. A distal hub element 3 of the catheter hub has a holding section 3a in which a catheter 4 is press-fitted. The proximal end of the hub element 3 has an enlarged diameter with regard to the distal end and forms a connecting section with a hub element 5 whose distal end overlaps the proximal end of the hub element 3 and which is provided at its proximal end with a Luer thread 6. Between the two hub elements 3 and 5, a check valve in the form of a valve disc 7 is inserted and is fixed in place by the two hub elements 3 and 5.

Figures 3, 4:
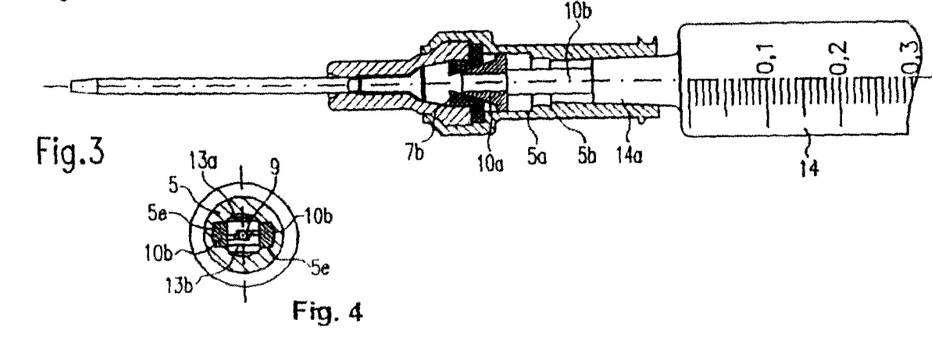
FIG. 3 shows the device with an attached syringe.
FIG. 4 shows a sectional view along the line A-A in FIG. 1.

In the ready position according to FIG. 1, there is inserted in the catheter hub 2 a needle hub 8 to which a hollow needle 9 is fixed which extends through the valve disc 7 and the catheter 4 so that the needle tip 9a is exposed. Between needle hub 8 and valve disc 7 there is displaceably arranged in the proximal hub element 5 a valve actuating element 10 which has a nose section with a truncated cone-shaped locating section 10a which serves to open the valve disc 7, as FIG. 3 shows. On the proximal side, a plunger section 10b adjoins the locating section 10a and has a hollow space or a gap for receiving a needle guard element 13. In the embodiment shown, the plunger section 10b is formed by two spaced plungers between which the needle guard element in the form of a spring clip 13 is inserted, as shown in the cross-sectional view in FIG. 4.

Figure 6:
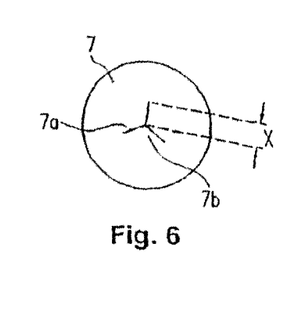
FIG. 6 shows a view of the valve disc.

On withdrawal of the hollow needle 9 from the catheter hub 2, an engaging means 9b (FIG. 2), provided near the needle tip 9a and having the form of a radial projection on the hollow needle which can be formed by light crimping, engages with the outer circumference of a bore in the rear wall 13c of the spring clip 13, so that the spring clip 13 is removed from the catheter hub with the needle 9, while simultaneously resilient portions or the spring arms 13a and 13b of the spring clip cover the needle tip, completely protecting and blocking it in a needle guarded position. In this separated position shown in FIG. 2, the valve disc 7, due to its elasticity, closes the through-hole for the hollow needle 9 so that no blood can flow out through the catheter 4. As FIG. 6 shows, the valve disc is provided for example with three slits 7a starting from the middle and extending radially over a short section X, forming elastic flaps 7b therebetween which can be expanded by the hollow needle.

FIG. 3 shows the insertion of a syringe 14 in the catheter hub 2, wherein the neck portion 14a of the syringe comes to abut on the plunger section 10b of the valve actuating element 10 and presses it against the valve disc 7, so that the truncated cone-shaped locating section 10a outwardly displaces the flaps 7b of the valve disc and thereby opens the valve, so that a liquid can be inserted from the syringe 14 into the catheter 4 by passing through a bore of the nose section and the gap of the plunger section.

The incline of the truncated cone on the locating section 10a and the displacement path of the actuating element 10 relative to the valve disc 7 are designed such that due to the elasticity of the material of the valve disc 7, the flaps 7b displace the locating section 10a to the right in FIG. 3 when the syringe 14 is removed from the catheter hub 2. Hereby, the valve disc 7 is automatically closed, as the position in FIG. 2 shows.

Figure 2:
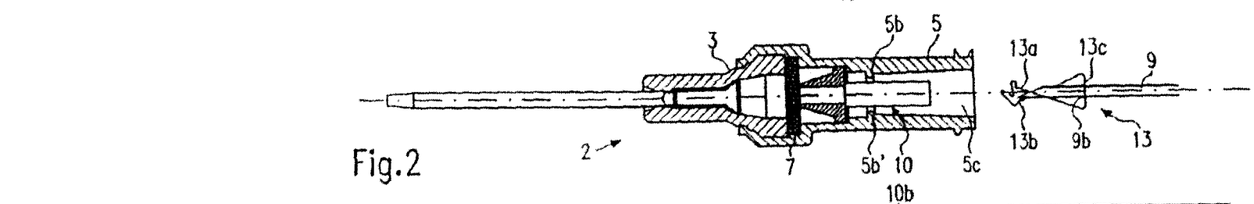
FIG. 2 shows the catheter insertion device with the hollow needle removed.

In the hub element 5, there is formed by a shoulder 5a a stop for the actuating element 10, to define the position of the actuating element in the separated position in FIG. 2. The shoulder 5a can stop a projection that extends radially of the lengthwise axis of the valve actuator Hereby, the truncated cone-shaped locating section 10a lies near the stop 5a, while its distal end abuts on the valve disc 7 as shown in FIG. 2. The radial slits 7a of the valve disc 7 are designed such that in the ready position in FIG. 1, the flaps 7b are bent radially upwards less than in the open position by the locating section 10a in FIG. 3.

As the cross-sectional view in FIG. 4 shows, the two plungers 10b of the valve actuating element 10 are guided in longitudinal grooves 5e of the hub element 5 and they project radially inwards into the bore 5c of the hub element 5, so that they form an abutting surface for the neck portion 14a of the syringe 14. The bore 5c in the hub element 5 is formed slightly conically corresponding to the conical neck portion 14a of a syringe.

On the inner circumference of the bore 5c of the hub element 5, a further shoulder 5b having a smaller diameter is formed, on which the radially outer areas of the spring arms 13a and 13b abut in the ready position in FIG. 1. Hereby, the spring clip 13 is fixed in its position in the hub element 5. When the needle hub 8 with the hollow needle 9 is removed from the catheter hub 2, first the spring clip 13 is held on the shoulder 5b by abutting until the radial projection 9b comes to abut on the rear wall 13c of the spring clip. In this position, the two spring arms 13a, 13b can be released from the shoulder 5b and spring back inwards so that surfaces on the two spring arms cover the needle tip, as FIG. 2 shows, whereupon the spring clip 13 with the hollow needle 9 can be removed from the catheter hub. As shown in FIG. 2, walls having surfaces at distal ends of the spring arms are moved distal of the needle tip to cover the needle tip.

In the embodiment according to FIGS. 1 to 3, the distal end section of the hub element 5 is shrunk, welded or bonded onto the proximal end section of the hub element 3 after the valve actuating element 10 and the valve disc 7 are inserted in the hub element 5. It is also possible to join the two hub elements 3 and 5 to one another, for example by a thread which is secured against loosening after assembly. The spring clip 13 is inserted together with the hollow needle 9 in the bore 5c of the hub element 5 during assembly, wherein the radially outer areas of the spring arms 13a, 13b snap in at the shoulder 5b under elastic deformation.

Preferably, in front of the shoulder 5b a projection 5b' can be formed in the bore 5c of the hub element, as shown in FIG. 2. Hereby the snap-in and holding effect of the spring clip 13 is increased.

Figure 5:
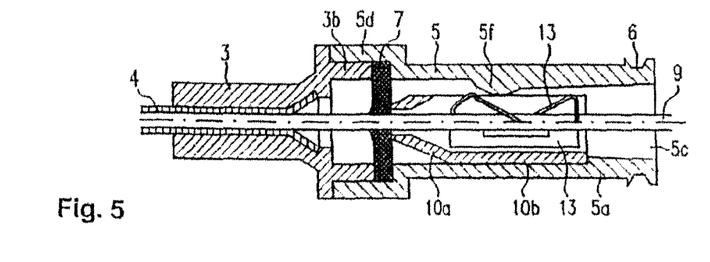
FIG. 5 shows a longitudinal section through another embodiment.

FIG. 5 shows a modified embodiment of the connection of the two hub elements 3 and 5, in which two cylindrical sections 3b and 5d engage in one another. A thread can be provided between these two cylindrical sections. However, it is also possible to bond or weld these two sections.

Figure 7A:
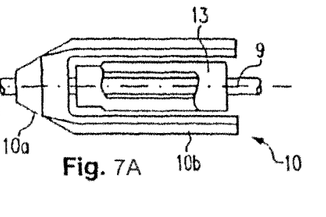
FIGS. 7A, 7B, 7C, 7D, and 7E show different views of a valve actuating element.
Figure 7B:
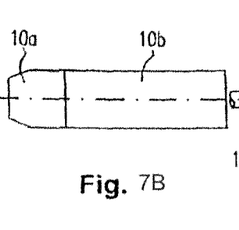
Figure 7C:
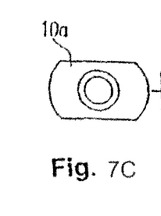
Figure 7D:
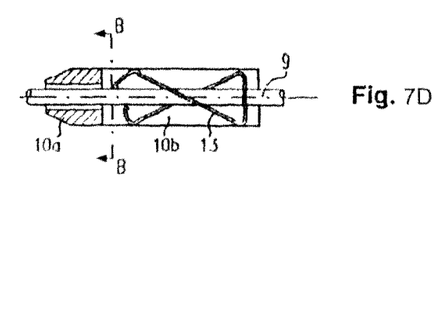
Figure 7E:
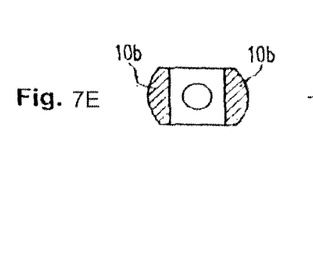

In this embodiment, the valve actuating element 10 is also modified in relation to the embodiment of FIGS. 1 to 3. FIG. 7A shows a side view of the approximately U-shaped actuating element 10 with the spring clip 13 inserted therein. As the side view rotated by 90° in FIG. 7B shows, the locating section 10a is partly flattened on opposite sides so that the width of the plunger sections 10b extends into the locating section 10a. FIG. 7C is a front view from the left in FIG. 7B and shows the flattened structure of the locating section 10a. FIG. 7D is a sectional view along the central line in FIG. 7B. FIG. 7E shows a section through the valve actuating element 10 along the line B-B in FIG. 7D.

FIG. 5 shows the lower half of the valve actuating element 10 corresponding to the view in FIG. 7A, and the upper half in a sectional view rotated by 90° corresponding to FIG. 7B. The shoulder 5a for positioning the valve actuating element 10 in the hub element 5 is hereby formed on the ends of the diametrically opposite grooves 5e (FIG. 4), so that the proximal ends of the plunger sections 10b abut on the shoulders 5a. Corresponding to the shoulder 5b in FIGS. 1 to 3 in the embodiment in FIG. 5, there is formed on the hub element 5 a projection 5f which projects inwards at diametrically opposite positions on the bore 5c of the hub element 5 and fixes the spring clip 13 in the hub element 5 until the spring arms 13a, 13b spring inwards over the needle tip and the spring clip with the hollow needle 9 is removed from the catheter hub.

Figures 8, 9B:
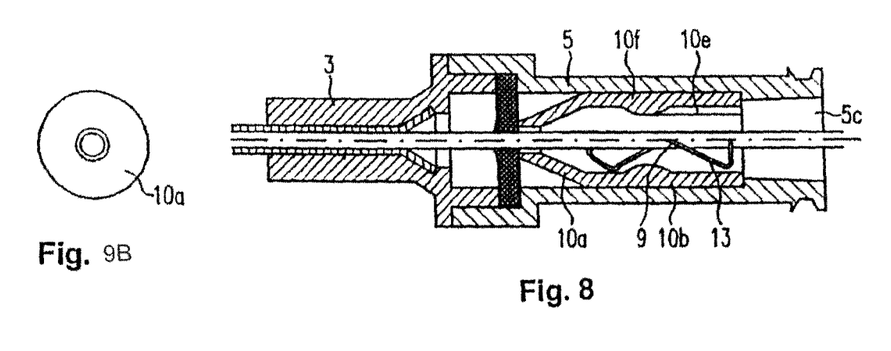
FIG. 8 shows a longitudinal section through a further embodiment.
FIGS. 9A and 9B show front views of the valve actuating element of FIG. 8.
Figure 9A:
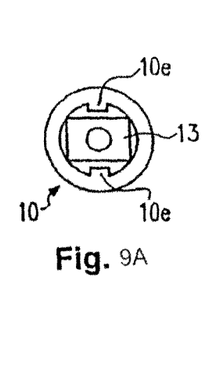

FIG. 8 shows a modified embodiment having a hollow cylindrical valve actuating element 10 on whose inner circumference a projection 10f is formed for positioning the spring clip 13 inside the valve actuating element 10. FIG. 9A shows a front view of the valve actuating element 10 from the right and FIG. 9B shows a front view from the left in FIG. 8, wherein for locating the neck portion 14a of a syringe 14, in this embodiment radially inwardly projecting ribs 10e are formed which protrude radially into the bore 5c of the hub element 5, as the upper half of the valve actuating element in FIG. 8 shows, in which the sectional view of the lower half of the valve actuating element 10 is shown rotated by 90° in relation to the upper half.

Figure 10:
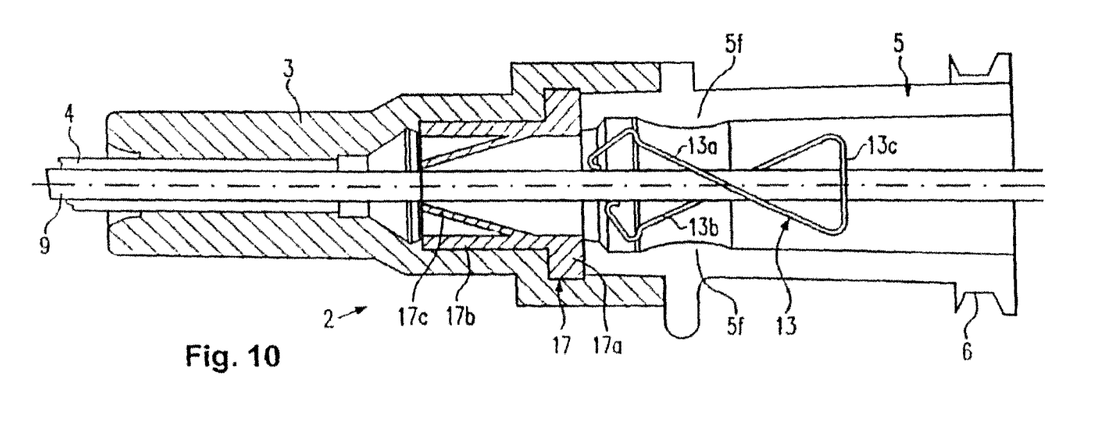
FIG. 10 shows a longitudinal section through a further embodiment.

FIG. 10 shows a modified embodiment wherein between the two hub elements 3 and 5 a check valve 17 is inserted, which has a hollow cylindrical section 17b starting from a flange section 17a and abutting on the inner circumference of the hub element 3. From the inner circumference near the flange section 17a there start two opposite flaps 17c, which abut on the outer circumference of the hollow needle 9 in the ready position in FIG. 10. When the needle 9 is removed from the catheter hub 2, the elastically deformed flaps 17c move inwards and close the valve. In this embodiment, an actuating element for opening the valve 17 is not necessary, because the pressure of the fluid from the syringe 14 displaces the flaps 17c radially outwards so that the liquid can flow out through the valve 17. In this embodiment of a check valve, a so-called duck-bill valve is concerned, whose construction is in itself known.

In FIG. 10, in order to allow the spring clip 13 to be held in the catheter hub during withdrawal of the hollow needle 9 from the catheter hub 2 until the radial projection 9b on the hollow needle engages with the rear wall 13c to cover the needle tip, in this embodiment there is formed on the inner circumference of the proximal hub element 5 a projection 5f which extends radially inwards and on which the radially outer areas of the spring arms 13a and 13b come to abut and hold the spring clip until the spring arms spring back radially inwards to cover the needle tip. The inner diameter of the projection 5f is designed only slightly smaller than the maximum radial dimension at the spring arms 13a and 13b, so that during assembly the spring clip 13 can be inserted by slight pressure into the position in the catheter hub as shown in FIG. 10.

In the embodiment of a catheter insertion device according to FIGS. 1 to 9, in the position of the valve actuating element 10 in FIG. 2 the valve disc 7 can be opened by low pressure produced by the syringe 4 for drawing off liquid from the catheter, wherein the elastic flaps 7b are bent upward by the low pressure. In the embodiment of FIG. 10, a drawing-off of liquid from the catheter is not possible, because the duck-bill valve does not open when there is low pressure on the proximal side.

It is convenient to fabricate the check valve in the form of a valve disc 7 or of the flap valve 17 from elastic silicon, while a correspondingly rigid plastic material is used for the hub elements 3 and 5 and for the valve actuating element 10.

What is claimed is:
1. A catheter insertion device comprising:
   a catheter hub comprising a body having an interior surface defining a bore with a Luer taper, a shoulder inside the bore and distal of a proximal opening to the bore, and a catheter tube attached at a distal end of the catheter hub;

a valve comprising at least one slit located inside the bore of the catheter hub for limiting fluid flow through the bore and remaining inside the bore in a ready position and a needle guarded position;

a valve actuator slidably disposed in the bore of the catheter hub; said valve actuator comprising a nose section, a bore, a projection extending radially of a lengthwise axis of the valve actuator, and a plunger section comprising plunger components located proximally of the nose section, said plunger section comprising a gap between the plunger components to permit fluid flow through the gap and the bore of the valve actuator, wherein said plunger section comprises an abutting surface at a proximal end for pushing by a male Luer tip when said male Luer tip is located in said bore of said catheter hub;

a needle having a needle shaft defining a needle axis projecting distally of an end of a needle hub and through the catheter tube with a needle tip of the needle shaft extending out a distal end opening of the catheter tube; and a needle guard comprising a surface for guarding the needle tip from unintended needle sticks when the needle tip is removed from the catheter hub, said surface of the needle guard being located to a side of the needle shaft in the ready position and being located distal of the needle tip in the needle guarded position to guard the needle tip.

2. The catheter insertion device of claim 1, wherein the bore of the valve actuator extends through the nose section and the needle shaft is located in the bore that extends through the nose section in the ready position.

3. The catheter insertion device of claim 2, wherein the valve actuator and the needle are slidable relative to one another.

4. The catheter insertion device of claim 3, wherein the needle guard and the needle are slidable relative to one another.

5. The catheter insertion device of claim 1, wherein the needle guard is biased by the side of the needle shaft in the ready position.

6. The catheter insertion device of claim 1, wherein the needle comprises a lateral projection for engaging a perimeter defining an opening on a proximal wall of the needle guard.

7. The catheter insertion device of claim 1, wherein the catheter hub comprises a first hub section attached to a second hub section.

8. The catheter insertion device of claim 1, wherein the valve comprises the at least one slit comprising three slits defining three flaps.

9. A method for assembling a catheter insertion device comprising:

forming a catheter hub comprising a body having an interior surface defining a bore with a female Luer, a shoulder on the interior surface and distal of a proximal opening to the bore, and a catheter tube attached at a distal end of the catheter hub;

positioning a valve with at least one slit inside the bore of the catheter hub for blocking fluid flow through the bore, said valve being located inside the bore in a ready position and in a needle guarded position;

positioning a valve actuator having a lengthwise axis slidingly in the bore of the catheter hub; said valve actuator comprising a nose section, a bore, a projection extending radially of the lengthwise axis, and a plunger section located proximally of the nose section and wherein said plunger section comprises a gap to permit fluid flow to flow through the gap and through the bore of the valve actuator;

projecting a needle having a needle shaft defining a needle axis distally of an end of a needle hub and projecting the needle shaft through the catheter tube and the at least one slit so that a needle tip of the needle extends out a distal opening of the catheter tube;

mounting a needle guard around said needle such that said needle guard and said needle are slidable relative to one another; wherein said needle guard comprises a surface for guarding the needle tip from unintended needle sticks when the needle tip is removed from the catheter hub; and wherein the nose section of the valve actuator is slidable into the valve to open the at least one slit when a male Luer tip is located in said bore of said catheter hub and pushing distally against an abutting surface at a proximal end of the valve actuator.

10. The method of claim 9, wherein the catheter hub comprises a push tab on an exterior of the body.

11. The method of claim 9, wherein the plunger section comprises two spaced apart plunger components.

12. The method of claim 9, wherein the surface of the needle guard is located to a side of the needle in the ready position.

13. The method of claim 12, wherein the needle and the needle guard are movable relative to one another so that the surface is distal of the needle tip in the needle guarded position to guard the needle tip.

14. The method of claim 9, wherein the bore of the catheter hub comprises a groove and wherein the valve actuator is positioned at least in part in the groove.

15. The method of claim 9, wherein the needle guard is located distally of the proximal opening of the catheter hub.

16. The method of claim 9, further comprising moving the nose section of the valve actuator into the valve by positioning a male Luer tip in the proximal opening of the bore of the catheter hub.

17. The method of claim 16, further comprising removing the male Luer tip from the proximal opening of the bore of the catheter hub for allowing the valve to close.

18. A catheter insertion device comprising:

a catheter hub comprising a body with an interior defining a bore having a female Luer at a proximal end and an internal shoulder;

a catheter tube with a distal end opening, said catheter tube attached to and extending distally of the catheter hub;

a needle having a needle shaft with a needle tip, said needle shaft projecting distally of an end of a needle hub and through the catheter tube with the needle tip located distally of the distal end opening of the catheter tube;

a valve with at least one slit sized and shaped to obstruct fluid flow, said valve being positioned inside the bore of the catheter hub and remaining inside the bore of the catheter hub when the needle is removed from the catheter hub;

a valve actuator having a lengthwise axis slidingly disposed in the bore of the catheter hub to actuate the valve, the valve actuator comprising a nose section structured to push the valve to open the at least one slit, wherein said valve actuator comprises a bore and a plunger section located proximally of the nose section, said plunger section comprising spaced apart plunger components having a gap to permit fluid flow to flow through the plunger components and the bore of the valve actuator;

a needle guard located proximally of the nose section, said needle guard comprising a surface located to a side of the needle shaft in the ready position and the needle guard and the needle movable relative to one another so that the surface is distal of the needle tip in a protected position to guard the needle tip from unintended needle sticks; and wherein the plunger section comprises an actuating surface that is exposed for abutting by a male Luer tip after the needle guard is removed with the needle from the catheter hub.

19. The catheter insertion device of claim 18, wherein the needle guard is located at least in part inside the bore of the catheter hub.

20. The catheter insertion device of claim 19, wherein the needle guard comprises two resilient arms.

21. The catheter insertion device of claim 20, wherein the needle guard is located between the spaced apart plunger components.

22. The catheter insertion device of claim 20, further comprising a radial projection on the needle for engaging a proximal wall on the needle guard when the needle is removed from the catheter hub.

23. The catheter insertion device of claim 18, wherein the nose section of the valve actuator has an exterior surface and a projection projects radially of the valve actuator and abuts the internal shoulder in the bore of the catheter hub.

24. The catheter insertion device of claim 18, wherein the valve actuator is slidable distally when pushed by a male Luer tip and is slidable proximally when the male Luer tip is removed.

25. The catheter insertion device of claim 18, further comprising a groove and wherein the valve actuator is disposed at least in part in the groove.

26. A catheter insertion device comprising:

a catheter hub comprising a body with an interior defining a bore having a female Luer at a proximal end, a groove, and a shoulder;

a catheter tube comprising a distal end opening, said catheter tube extending distally of the catheter hub;

a needle having a needle shaft with a needle tip, said needle projecting distally of an end of a needle hub and through the catheter tube with the needle tip located distally of the distal end opening of the catheter tube in a ready position;

a valve with at least one slit positioned inside the bore of the catheter hub, said valve having a surface to obstruct fluid flow and remaining inside the bore of the catheter hub when the needle is removed from the catheter hub;

a valve actuator having a lengthwise axis slidingly disposed in the bore of the catheter hub to actuate the valve, the valve actuator comprising a nose section structured to push the valve to open the at least one slit, a bore, and a plunger section comprising spaced apart plunger components extending proximally of the nose section and having a gap to permit fluid flow through the plunger components and the bore of the valve actuator;

a needle guard comprising a surface mounted with the needle so that the needle tip is guarded by the surface of the needle guard when the needle tip is moved from the ready position to a protected position; and wherein the plunger section is guided distally within the groove when a male Luer tip is positioned in the bore of the catheter hub and pushing against an abutting surface at a proximal end of the valve actuator.

27. The catheter insertion device of claim 26, wherein the needle guard is located at least in part inside the bore of the catheter hub.

28. The catheter insertion device of claim 27, wherein the needle guard comprises an arm that is movable relative to the needle.

29. The catheter insertion device of claim 28, wherein a projection on the valve actuator is located distally of the shoulder in the bore of the catheter hub.

30. The catheter insertion device of claim 26, wherein the needle guard is located between the spaced apart plunger components.

* * * * *

UNITED STATES PATENT AND TRADEMARK OFFICE
CERTIFICATE OF CORRECTION

PATENT NO. : 10,166,370 B2
APPLICATION NO. : 16/004211
DATED : January 1, 2019
INVENTOR(S) : Woehr et al.

It is certified that error appears in the above-identified patent and that said Letters Patent is hereby corrected as shown below:

In the Specification

In Column 2, Line 61, after "actuator" insert -- . --.

In Column 3, Line 2, delete "lob" and insert -- 10b --, therefor.

Signed and Sealed this
Sixteenth Day of August, 2022

Katherine Kelly Vidal
*Director of the United States Patent and Trademark Office*